(12) United States Patent
Matsuo et al.

(10) Patent No.: US 6,492,307 B1
(45) Date of Patent: Dec. 10, 2002

(54) PERSONAL CLEANSING SHEET

(75) Inventors: Keiko Matsuo, Tokyo (JP); Toshio Yamazaki, Tokyo (JP); Takashi Kawai, Tochigi (JP); Manabu Kaneda, Tochigi (JP)

(73) Assignee: Kao Corporation, Tokyo (JP)

( * ) Notice: Subject to any disclaimer, the term of this patent is extended or adjusted under 35 U.S.C. 154(b) by 83 days.

(21) Appl. No.: 09/612,416

(22) Filed: Jul. 7, 2000

(30) Foreign Application Priority Data

| Jul. 8, 1999 | (JP) | ............................................ 11-195145 |
| Feb. 9, 2000 | (JP) | ........................................ 2000-038110 |
| Apr. 5, 2000 | (JP) | ........................................ 2000-103498 |

(51) Int. Cl.[7] .............................................. C11D 17/04
(52) U.S. Cl. ........................ 510/120; 510/130; 510/137; 510/439; 428/286
(58) Field of Search .................................. 510/120, 130, 510/137, 439; 428/286, 284, 287, 903

(56) References Cited

U.S. PATENT DOCUMENTS

| 3,916,447 A | * | 11/1975 | Thompson | ........................ 2/46 |
| 4,436,780 A | * | 3/1984 | Hotchkiss et al. | ............. 428/198 |
| RE31,885 E | * | 5/1985 | Meitner | ........................ 428/156 |
| 4,753,843 A | * | 6/1988 | Cook et al. | ................ 428/286 |
| 4,863,785 A | * | 9/1989 | Berman et al. | ............. 428/218 |
| 4,904,521 A | * | 2/1990 | Johnson et al. | ............. 428/284 |
| 4,906,513 A | * | 3/1990 | Kebbell et al. | ............. 428/198 |
| 5,039,431 A | * | 8/1991 | Johnson et al. | ............. 264/113 |
| 5,204,165 A | * | 4/1993 | Schortmann | ................. 428/198 |
| 5,466,513 A | * | 11/1995 | Wanek et al. | ............... 428/218 |
| 5,466,516 A | * | 11/1995 | Lutzow et al. | .............. 428/282 |
| 5,658,577 A | * | 8/1997 | Fowler et al. | ............... 424/401 |
| 5,763,332 A | * | 6/1998 | Gordon et al. | ................. 442/84 |
| 5,766,737 A | * | 6/1998 | Willey et al. | ............... 428/198 |
| 5,908,707 A | * | 6/1999 | Cabell et al. | ............. 428/537.5 |
| 6,214,362 B1 | * | 4/2001 | Page | ........................... 424/402 |
| 6,221,382 B1 | * | 4/2001 | Ishida et al. | ................. 424/443 |

FOREIGN PATENT DOCUMENTS

| EP | 0870496 A2 | * | 10/1998 |
| EP | 0997142 A1 | * | 5/2000 |
| JP | 11-239517 | | 7/1999 |
| WO | WO 98/44185 A1 | * | 10/1998 |

\* cited by examiner

*Primary Examiner*—Lorna M. Douyon
(74) *Attorney, Agent, or Firm*—Oblon, Spivak, McClelland, Maier & Neustadt, P.C.

(57) ABSTRACT

A personal cleansing sheet with which the skin and hair can be easily cleansed of oily soils such as sebum and aqueous soils such as sweat or salts, has a structure in which an oily substance absorption layer that serves as a region that absorbs oil substances is laminated with an aqueous cleansing liquid retention layer that serves as a region that retains an aqueous cleansing liquid.

22 Claims, 3 Drawing Sheets

PERSONAL CLEANSING SHEET

BACKGROUND OF THE INVENTION

1. Field of the Invention

The present invention relates to a personal cleansing sheet with which the skin and hair can be easily cleansed of oily soils such as sebum or aqueous soils such as sweat or salts, and more particularly relates to a personal cleansing sheet with which the skin and hair can be easily cleansed without smudging makeup such as foundation.

2. Description of the Related Art

Skin cleansing sheets for removing soils adhering to the hair and skin, and particularly the face, have been commercially available in recent years. These skin cleansing sheets fall into two major categories, oil absorbent dry sheets used primarily for removing oily soils such as sebum, and wet sheets that retain an aqueous cleansing liquid and are used primarily for removing aqueous soils such as sweat or salts.

Typical examples of oil absorbent dry sheets include: sheets produced by subjecting a fibrous raw material such as natural pulp, paper mulberry, mitsumata, or hemp to a papermaking process, and then making this sheet thin by calendering or the like; and soft plastic films having numerous micropores on the surface. These dry sheets can be used to absorb and remove oily soils such as sebum or cosmetics that stand on the surface of the underlying makeup (such as foundation) without smudging the makeup, thereby preventing undesired shine.

A wet sheet that retains an aqueous cleansing liquid is generally produced by impregnating a nonwoven fabric of hydrophilic fibers with an aqueous cleansing liquid. If needed, a powder that makes the skin feel smooth and dry can be adhered to a surface of the sheet. Such a wet sheet allows aqueous soils such as sweat or salts that stand on the surface of the underlying makeup (such as foundation) to be removed without smudging the makeup, and allows the user to enjoy refreshing feel similar to one felt upon washing the face.

A problem with the above-mentioned oil absorbent dry sheets, however, was that they are unable to remove aqueous soils such as sweat or the salts and water-soluble proteins contained therein. A problem encountered with the above-mentioned wet sheets that retained an aqueous cleansing liquid, on the other hand, was that they were unable to remove oily soils sufficiently, and were therefore unable to adequately prevent shine or smudging.

SUMMARY OF THE INVENTION

It is an object of the present invention to allow oily soils such as sebum and aqueous soils such as sweat or salts to be removed with ease from the skin and hair.

The inventors arrived at the present invention upon discovering that the stated object can be achieved by incorporating into a single sheet material an oil absorbent region that absorbs and removes oily soils and an aqueous cleansing liquid retention region that wipes away or absorbs and removes aqueous soils.

Specifically, the present invention provides a personal cleansing sheet having a region that absorbs oily substances and a region that retains an aqueous cleansing liquid. Here, the region that absorbs oily substances may constitute one side of the sheet and the region that retains an aqueous cleansing liquid may constitute the other side, or the region that absorbs oily substances and the region that retains an aqueous cleansing liquid may both be on the same side.

DESCRIPTION OF THE PREFERRED EMBODIMENTS

Embodiments of the personal cleansing sheet of the present invention will be described by referring to the figures.

Figure 1:
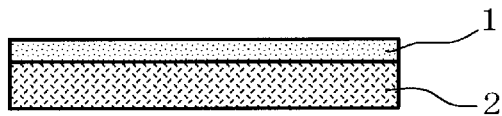
FIG. 1 is a cross-sectional view of an embodiment of the personal cleansing sheet of the present invention.
Figure 2:
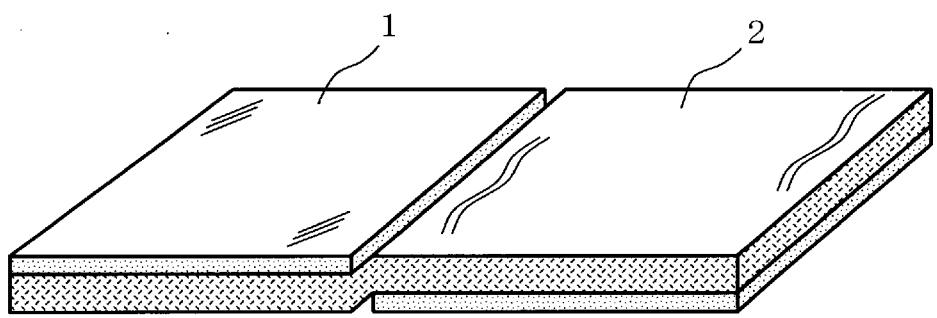
FIG. 2 is a perspective view of an embodiment of the personal cleansing sheet of the present invention.
Figure 3A:
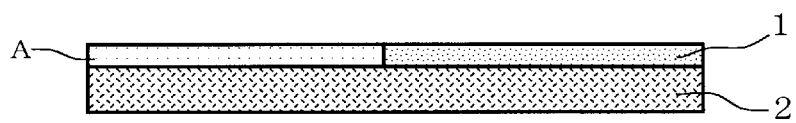
FIGS. 3A, 3B, and 3C are cross-sectional views of embodiments of the personal cleansing sheet of the present invention.
Figure 3B:
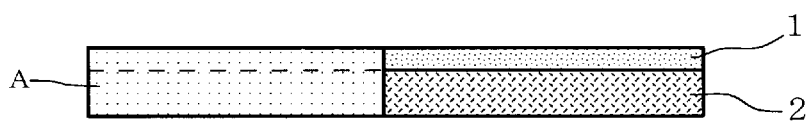
Figure 3C:
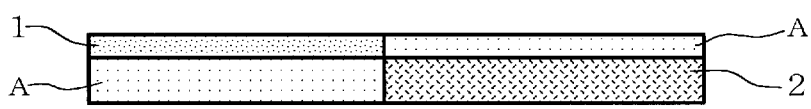

The personal cleansing sheet in FIG. 1 has a structure in which an aqueous cleansing liquid retention layer 2 (a region that retains an aqueous cleansing liquid) is laminated on one side of an oily substance absorption layer 1 (a region that absorbs oily substances). In this case, as shown in FIG. 2, one oily substance absorption layer 1 may be laminated over half of the surface of the aqueous cleansing liquid retention layer 2, and another oily substance absorption layer 1 may be laminated under the other half. The oily substance absorption layer 1 and aqueous cleansing liquid retention layer 2 should constitute at least part of one side of the personal cleansing sheet. As shown in FIGS. 3A, 3B, and 3C, a function layer A (such as a foundation-containing layer, perfume-containing layer, puff layer, handle layer, or the like having a substrate of woven or nonwoven fabrics, a sponge, a brush, paper, or the like) may be combined on part of either or both of the sides of the sheet, besides the oily substance absorption layer 1 and aqueous cleansing liquid retention layer 2. Depending on the type of function layer A, a variety of functions can be imparted to the personal cleansing sheet in this way. When a dried, hydrophilic nonwoven fabric layer is combined as the function layer A, for instance, the cleansing ability of the personal cleansing sheet may further be enhanced. This also prevents soils that have been removed with the personal cleansing sheet from re-adhering to the hands.

Figure 4:
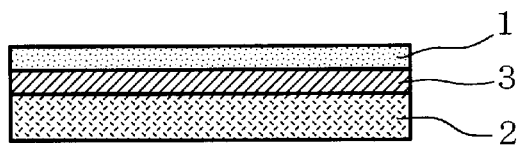
FIG. 4 is a cross-sectional view of an embodiment of the personal cleansing sheet of the present invention.

As a modification of the above-mentioned embodiments, a liquid impermeable layer 3, as that shown in FIG. 4, may be laminated between the oily substance absorption layer 1 and aqueous cleansing liquid retention layer 2.

Figure 5:
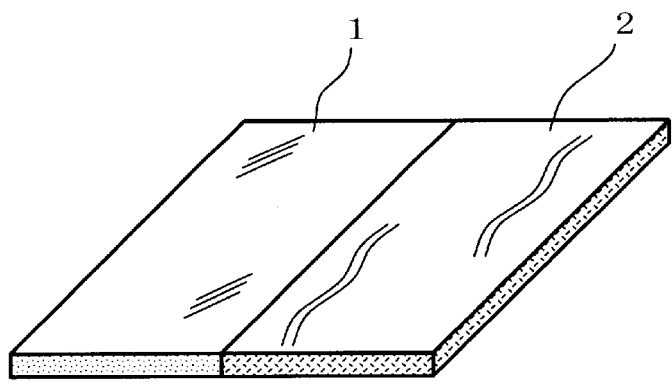
FIG. 5 is a perspective view of an embodiment of the personal cleansing sheet of the present invention.
Figure 6:
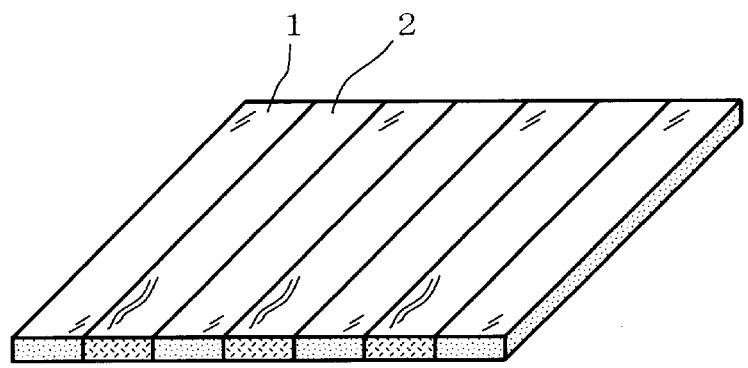
FIG. 6 is a perspective view of an embodiment of the personal cleansing sheet of the present invention.
Figure 7:
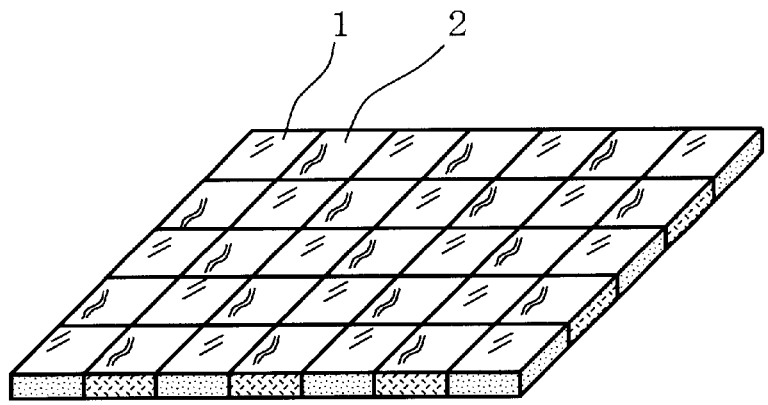
FIG. 7 is an oblique view of an embodiment of the personal cleansing sheet of the present invention.

As an additional embodiment, the personal cleansing sheet in FIG. 5 has a structure in which the oily substance absorption layer 1 (the region that absorbs oily substances) and the aqueous cleansing liquid retention layer 2 (the region that retains an aqueous cleansing liquid) are connected laterally so that the two layers appear on the same side. Alternatively, the two layers may be laid out in a vertical stripe pattern as shown in FIG. 6, or in a checkerboard pattern as shown in FIG. 7. With the embodiments in FIGS. 5 to 7, a substrate sheet may be laminated on one side of the personal cleansing sheet (not shown) in order to make the product easier to handle.

As the oily substance absorption layer 1 in the present invention, a woven or nonwoven fabric in the form of a sheet or film formed from lipophilic synthetic resins can be used.

Examples of the synthetic resin include thermoplastic resins, for example, polyolefin resins such as polyethylene, polypropylene, polybutylene, poly-4-methylpentene and ethylene-propylene block copolymers; polyester resins such as polyethylene terephthalate or polybutylene terephthalate; polyvinyl chloride resins; polyamide resins such as nylon; polyacrylic resins such as ethyl polyacrylate; polyurethane resins; cellulose resins; polylactic acid resins, or the like.

Additives can be added as needed to these thermoplastic resins in order to make the resins more lipophilic or more flexible. Examples of the additives include liquid rubbers such as butadiene oligomers or isoprene oligomers, petroleum resins, coumarone resins, chlorinated paraffins, silicone oils, liquid paraffin or polyethylene wax.

It is preferable for numerous pores to be formed in the oily substance absorption layer 1 in order to increase the surface area over which oily soils are absorbed. Examples of ways to form numerous pores in the oily substance absorption layer 1 include (i) processes in which inorganic fine particles such as clay, calcium carbonate or barium sulfate are dispersed in a thermoplastic resin, this mixture is made into a film by extrusion molding, and the film thus obtained is drawn uniaxially or biaxially, which forms pores in the vicinity of the inorganic fine particles, and (ii) a meltblowing process, in which a high-temperature and high-pressure air jet is blown into the outlet of a spinning nozzle in the melt spinning of a thermoplastic resin, which draws and opens up the just-spun fibers and makes them into ultrafine fibers, and these ultrafine fibers are gathered into a sheet on a collecting conveyor. If necessary, the product of these processes can then be subjected to a hot embossing treatment, calendering, or the like to adjust the porosity.

In the case of a porous film that has undergone the above-mentioned drawing, the porosity thereof is preferably about 5 to about 50%. The porosity is measured as the percentage of the filled amount when all of the pores in the porous film have been filled with the same thermoplastic resin as that of the film, to the amount of a film not having corresponding pores.

It is particularly preferable to use a nonwoven fabric that contains fibers of the above-mentioned lipophilic synthetic resins and is in the form of a sheet containing substantially no liquid. Such a nonwoven fabric quickly soaks up oily soils such as sebum through the capillary action produced between the fibers thereof. A nonwoven fabric is also gentler to the skin than a film. Therefore, the oily substance absorption layer 1 will remove oily soils better and will also feel better on the skin if it is composed of such a nonwoven fabric.

The amount in which the lipophilic synthetic fibers are contained in this nonwoven fabric is preferably at least about 5 wt %, and preferably at least about 30 wt %, more preferably about 50 wt % or more. The term "lipophilic" as used here means that the contact angle with respect to oil is small, and more specifically means that the contact angle with respect to oil as measured by the drop method is no more than about 50°, and preferably no more than about 30°. The contact angle by the drop method corresponds to the angle that is measured when a drop of liquid (squalane as model sebum) is placed on the nonwoven fabric made solely of synthetic fibers of interest. The measurement is made through a microscope in which the cursor line is lined up with the contact point, i.e., the point at which the surface of the drop touches the nonwoven fabric.

A nonwoven fabric suited to the oily substance absorption layer 1 contains substantially no liquid. The term "liquid" as used here means a lotion having a sebum removal effect, which is a liquid containing as a main ingredient water or a lower alcohol. The phrase "contains substantially no liquid" (the liquid defined above) means that the liquid content is no more than about 5%, using as a reference the weight when the nonwoven fabric is left in a test room under standard conditions (a temperature of 20° C. and a humidity of 65%) to bring the moisture content of the fabric to equilibrium.

If the air permeability of the nonwoven fabric used as the oily substance absorption layer 1 is too low, the fabric will not feel good on the skin similar to the case of a film. The oily soil removal performance based on capillary action between the fibers will suffer if the air permeability is too high. Thus, the air permeability is preferably adjusted to between about 0.00005 and about 3 m/kPa.S, and more preferably between about 0.0005 and about 0.2 m/kPa.S. The air permeability here is measured using a commercially available air permeability measurement device (KES-F8-AP1, made by Kato Tech) in a test room with a temperature of about 20° C. and a humidity of about 65%.

If the coefficient of static friction of the nonwoven fabric is too low, the fabric will be too slippery on the skin, making it more difficult to use. If this coefficient is too high, the fabric will cling to the skin uncomfortably. Thus, a coefficient of static friction in a range of about 0.2 to about 0.4 is preferred. The coefficient of static friction of the nonwoven fabric is here measured using a test piece measuring 75 mm×35 mm and a commercially available friction tester (type Heidon-10, made by Shinto Kagaku), at an average elevation rate of 10 degrees per 6 seconds and a load of 200 g.

The nonwoven fabric will have a difficulty in adequately removing oily soils if its basis weight is too low. The manufacturing cost will rise undesirably if this weight is too high. Thus, a basis weight in a range of about 10 to about 80 $g/m^2$ is preferable, with about 20 to about 55 $g/m^2$ being particularly preferable.

The nonwoven fabric will have a difficulty in adequately removing oily soils if its apparent density is too low. The nonwoven fabric will become undesirably hard if the apparent density is too high. Thus, an apparent density in a range of about 0.05 to about 0.7 $g/cm^3$ is preferable, with about 0.1 to about 0.6 $g/cm^3$ being particularly preferable.

The manufacturing cost will rise undesirably if the fibers that make up the nonwoven fabric are too small in diameter. If the fibers are too thick the fabric will not feel as good to the touch. Thus, the fibers with a diameter in a range of about 0.1 to about 10 $\mu$m is preferable, with about 1 to about 6 $\mu$m being particularly preferable.

In addition to lipophilic synthetic fibers, as long as the effect of the present invention is not compromised, the nonwoven fabric used as the oily substance absorption layer 1 can also contain cellulose resin fibers, polylactic acid resin fibers, or other hydrophilic resin fibers or natural fibers.

The thickness of the oily substance absorption layer 1 is preferably about 10 to about 500 $\mu$m, more preferably about 20 to about 300 $\mu$m.

When a nonwoven fabric is used as the oily substance absorption layer 1, it is preferable to use one having a porous structure in order to improve the removal of oily soils through the capillary action produced between the fibers. Examples of processes for preparing such a nonwoven fabric include the above-mentioned melt-blowing process, as well as flash spinning, a split fiber process, and others known in the art.

It is also preferable for a powder to be contained in the nonwoven fabric used as the oily substance absorption layer 1. The powder contained in the nonwoven fabric gets into the gaps between the fibers that make up the nonwoven fabric, and thereby shortens the distance between fibers, which improves the oily soil removal performance of the oily substance absorption layer 1 through capillary action. When this happens, the sebum or other oil (the oily soils) gets into the gaps between the fibers and the powder, and permeates throughout the thickness of the oily substance absorption layer 1. As a result, the refraction of the oily substance absorption layer 1 with respect to light becomes unidirectional, or the transmitted light moves straight ahead. This makes the portion of the oily substance absorption layer 1 that has absorbed oily soils more transparent than the other portions, and it is easier to visually confirm that sebum has been absorbed.

Inorganic or organic powders such as Silica fine particles or crystalline cellulose fine particles, respectively, can be used as the above-mentioned powder. Clay mineral powders such as bentonite or kaolin are particularly favorable. The particle diameter of the powder is preferably about 1 to about 30 µm.

The powder contained in the nonwoven fabric that makes up the oily substance absorption layer 1 will not have a satisfactory effect if it is contained in too small an amount. The material cost will be undesirably high if this amount is too large. Thus, the powder content in a range of about 1 to about 40 wt % based on the weight of the nonwoven fabric is preferable.

It is also preferable for the surface of the nonwoven fabric used as the oily substance absorption layer 1 to have been smoothed by calendering. When smoothed by calendering, the nonwoven fabric shows a larger difference in the transmissivity of light between the oily soil absorbent portion of the oily substance absorption layer 1 and the surrounding portion, which makes it easier to tell whether oily soils have been absorbed. As long as this visual confirmation is possible and oily soils can be sufficiently removed, there are no restrictions on the conditions such as temperature and pressure in the calendering.

There are no restrictions on the coloring of the oily substance absorption layer 1, but it is preferable for it to be darkly colored, because a dark color makes it easier to confirm that sebum has been absorbed.

The aqueous cleansing liquid retention layer 2 in the present invention retains an aqueous cleansing liquid capable of removing aqueous soils in a liquid retainable sheet capable of retaining such an aqueous cleansing liquid. The degree to which the aqueous cleansing liquid is retained here is preferably about 100 to about 500 wt % with respect to the liquid retainable sheet.

A nonwoven fabric of natural or synthetic fibers, for example, can be used as the liquid retainable sheet. Examples of the nonwoven fabric include a wet or dry pulp sheet or a nonwoven fabric composed of fibers of rayon, acetate, acrylic, polyester, polyethylene, polypropylene, polyurethane, polyamide, cotton, pulp, or the like, or a blend or a composite of two or more types of these fibers. Specific examples include a cellulose nonwoven fabric containing polyolefin short fibers, and a mixed nonwoven fabric of cellulose and acrylic or nylon containing polyolefin short fibers. Examples of processes for preparing such a nonwoven fabric include wet-type hydroentangling, dry-type hydroentangling, an air-laid web process, and thermal-bonding. Among these, wet-type hydroentangling and dry-type hydroentangling are particularly preferred in view of the softness and the intensity of the resulting nonwoven fabric.

In view of applicability to heat fusion with an adjacent layer (such as the liquid impermeable layer discussed below), it is preferable that the nonwoven fabric for the liquid retainable sheet contains thermoplastic resin fibers, particularly short forms of such fibers. Examples of preferred thermoplastic resin fibers include core-sheath composite fibers or side-by-side composite fibers of thermoplastic resins, with the core-sheath composite fibers being particularly preferred. Examples of the combination of thermoplastic resins suitable for the core-sheath composite fibers include the following: polypropylene as core and polyethylene as sheath, polyester as core and polyethylene as sheath, polyester as core and polyester as sheath, and polyester as core and polypropylene as sheath (herein, examples of the polyester include polyethylene terephthalate). It is particularly preferable to select thermoplastic resins so that the resin used as the core has a higher melting point than the resin used as the sheath. The above-mentioned combinations of thermoplastic resins are also suitable for the side-by-side core-sheath composite fibers.

From the standpoint of ensuring good retention of the aqueous cleansing liquid, it is preferable that the nonwoven fabric contains hydrophilic fibers, preferably in an amount of at least about 20 wt %.

The aqueous cleansing liquid of the aqueous cleansing liquid retention layer 2 can be any known lotion, cleansing liquid, emulsion, or the like. It is particularly preferable for a sebum dissolving component such as ethanol or a surfactant aqueous solution to be contained.

It is also preferable for the aqueous cleansing liquid to contain an insoluble powder that will make the user's skin feel smooth and dry and provide refreshment similar to one felt upon washing the face.

This insoluble powder can be any of a variety of powders that are insoluble in the aqueous cleansing liquid and oily soils and aqueous soils on the skin surface. Examples include inorganic powders such as silica, alumina, talc, kaolin, mica, micaceous titanium, zeolite, ultramarine, zinc oxide or iron oxide, and organic powders of polymers such as nylon, vinyl polymers, dimethylsilicone crosslinked elastomers, polymethyl methacrylate or methacrylate-alkylenedimethacrylate copolymers. These insoluble powders may be either porous or nonporous. Using a mixture of (i) a powder that improves the feel of the aqueous cleansing liquid retention layer on the skin with (ii) an oil absorbent powder such as a porous polymer or silica is particularly preferable because the good skin feel and the refreshing feel will both last longer.

In order for the aqueous cleansing liquid retention layer to feel better on the skin, it is preferable for the average particle diameter of the above-mentioned insoluble powder to be about 1 to about 30 µm.

The insoluble powder is preferably contained in an amount of about 1 to about 40 wt %, based on the weight of the aqueous cleansing liquid retainable sheet.

In order to effectively deliver the insoluble powder to the skin, it is preferable for the voids (that is, the average pore diameter) of the aqueous cleansing liquid retainable sheet to be small, for example, about 1 to about 30 μm, such that the powder is retained on or close to the surface of the liquid retainable sheet. To make these voids small, it is preferable for the liquid retainable sheet to be made from ultrafine fibers such as rayon or pulp, or from acrylic or rayon fibers that are readily fibrillated and readily split.

The thickness of the aqueous cleansing liquid retention layer 2 is preferably about 100 μm to about 5 mm, and more preferably about 200 μm to about 1 mm.

The liquid impermeable layer 3 is preferably used in order to prevent the aqueous cleansing liquid contained in the aqueous cleansing liquid retention layer 2 from seeping into the oily substance absorption layer 1 (strike-through), and to keep any oily soils absorbed by the oily substance absorption layer 1 from migrating to the aqueous cleansing liquid retention layer 2.

For the purpose of improving the feel of the personal cleansing sheet, it is preferable for this liquid impermeable layer 3 to be a sheet or film of a soft material, examples of which include sheets and films of thermoplastic resins, for example, polyolefin resins such as polyethylene, polypropylene or polyethylene-polypropylene blend polymers; polyester resins such as polyethylene terephthalate or polybutylene terephthalate; polyvinyl chloride resins; polyamide resins such as nylon; polyacrylic resins such as ethyl polyacrylate; polyurethane resins; cellulose resins; or polylactic acid resins. Suitable additives can also be added to these sheets and films of thermoplastic resins for the purpose of making them more lipophilic or improving their flexibility. Examples of such additives include liquid rubbers such as butadiene oligomers or isoprene oligomers, petroleum resins, coumarone resins, chlorinated paraffins, silicone oils, liquid paraffin, or polyethylene wax.

The thickness of the liquid impermeable layer 3 is preferably about 5 to about 300 μm, with about 10 to about 200 μm being particularly preferable.

As to the relationship between the thermoplastic resin fibers contained in the aqueous cleansing liquid retainable sheet and the thermoplastic resin that makes up the liquid impermeable layer 3, in terms of securely bonding the two together by heating, it is preferable for them to have similar molecular structures (the same main structures) and to be substances that exhibit good miscibility with each other. It is more preferable for the molecular structures to be identical.

In a preferred embodiment of the personal cleansing sheet of the present invention described above, the oily substance absorption layer is a polypropylene melt-blown nonwoven fabric, the liquid impermeable layer is a polypropylene-polyethylene blend polymer film, and the liquid retainable sheet for the aqueous cleansing liquid retention layer is a wet-type hydroentangled nonwoven fabric of acrylic short fibers and pulp, containing core-sheath composite short fibers (polypropylene core and polyethylene sheath). Bonding between the aqueous cleansing liquid retention layer and the liquid impermeable layer will be inadequate here if the proportion in which the core-sheath composite short fibers are admixed into the wet-type hydroentangled nonwoven fabric is too small. The aqueous cleansing liquid retention layer will be stiff and not feel good on the skin if this proportion is too large. Thus, the proportion of the core-sheath composite short fibers is preferably about 5 to about 50 wt % based on the weight of the liquid retainable sheet. With this embodiment, lamination by heating is easy and there will be no separation between the fused layers with normal use. Furthermore, the overall personal cleansing sheet can be made thinner and more comfortable to use.

In the personal cleansing sheet of the present invention, each of the layers may be colored in order to make it easier to tell whether oily soils have been absorbed. It is preferable for the layers to be in different colors, and particularly for the color of the liquid impermeable layer to be darker than the color of the oily substance absorption layer so as to provide a clear contrast.

The personal cleansing sheet of the present invention shown in FIG. 1 can be manufactured by using a hot melt adhesive to laminate the oily substance absorption layer 1 to a liquid retainable sheet used for the aqueous cleansing liquid retention layer 2, then impregnating the liquid retainable sheet with an aqueous cleansing liquid by spraying, thereby producing the aqueous cleansing liquid retention layer 2. It can also be manufactured by bonding part of the oily substance absorption layer 1 to part of the liquid retainable sheet by heating, then impregnating the liquid retainable sheet with an aqueous cleansing liquid by spraying, thereby producing the aqueous cleansing liquid retention layer 2. The lamination of the oily substance absorption layer 1 and the liquid retainable sheet used for the aqueous cleansing liquid retention layer 2 is not limited to the examples given above. It may be accomplished by utilizing melt lamination. Alternatively, direct lamination may be performed in the course of manufacturing the constituent nonwoven fabrics.

The personal cleansing sheet of the present invention shown in FIG. 4 can be manufactured, for example, by using a hot melt adhesive to laminate an oily substance absorbent nonwoven fabric to a liquid impermeable thermoplastic resin film, and the thermoplastic resin film to an liquid retainable nonwoven fabric, then impregnating the liquid retainable nonwoven fabric with an aqueous cleansing liquid by spraying. Spraying with an aqueous cleansing liquid that contains a powder allows the powder to be placed efficiently on the surface of the liquid retainable nonwoven fabric.

When the personal cleansing sheet of the present invention is manufactured as above, it is preferable that before the liquid retainable sheet is sprayed and impregnated with the aqueous cleansing liquid, at least adjacent layers have been made to contain the same type of thermoplastic substance and are bonded by heating. Therefore, the oily substance absorbent nonwoven fabric, the liquid impermeable thermoplastic resin film, and the liquid retainable nonwoven fabric may be made to contain the same type of thermoplastic substance.

Alternatively, one type of thermoplastic substance (first thermoplastic substance) may be contained in the oily substance absorbent nonwoven fabric and the liquid impermeable thermoplastic resin film, and another type of thermoplastic substance (second thermoplastic substance) may be contained in the liquid impermeable thermoplastic resin film and the liquid retainable nonwoven fabric. In the latter case, the liquid impermeable thermoplastic resin film contains both the first thermoplastic substance and the second thermoplastic substance.

In the lamination of the layers, they may be adhesively bonded over the entire surfaces being bonded together. However, partial bonding is preferred in order to make the personal cleansing sheet more flexible and feel softer to the touch.

The personal cleansing sheets in the embodiments depicted in FIG. 2, FIGS. 3A to 3C, and FIGS. 5 to 7 can be manufactured basically in the same manner as the personal cleansing sheet in FIG. 1.

The personal cleansing sheet of the present invention is normally stored in a sealed pouch until it is used. Upon use, when it is then taken out of the sealed pouch. For instance, in the case of the personal cleansing sheets in FIGS. 1 to 4, oily soils such as sebum that has stood on the surface of the skin, hair, or makeup is absorbed and removed with the oily substance absorption layer side, and then any aqueous soils are removed with the aqueous cleansing liquid retention layer side. Therefore, with the personal cleansing sheet of the present invention, both oily soils and aqueous soils that rise to the surface of the skin or hair or the surface of makeup can be easily removed by using the both sides of a single sheet, without smudging makeup. This means that makeup will last much longer. With the personal cleansing sheets shown in FIGS. 5 to 7, oily soils and aqueous soils can be easily removed without having to turn the sheet over, by using different areas within a single side of the sheet.

Also, since a single personal cleansing sheet comprises both an oily substance absorption layer and an aqueous cleansing liquid retention layer, when a certain oily substance absorption layer is used, the flexibility and elasticity thereof can be adjusted by selecting the type of aqueous cleansing liquid retention layer. This allows the oily substance absorption layer to conform better to the skin, and allows oily soils to be removed efficiently.

Figure 8A:
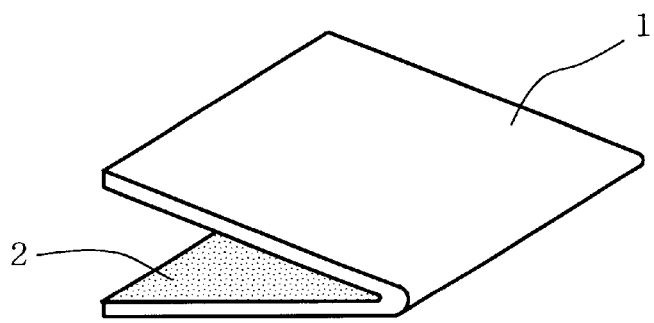
FIGS. 8A and 8B are explanatory diagrams of how the personal cleansing sheet of the present invention can be folded for the storage in a sealed pouch.
Figure 8B:
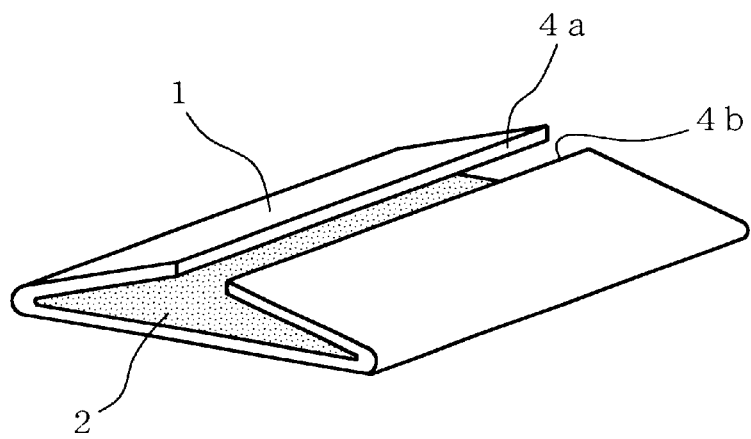

Particularly preferable ways to store the personal cleansing sheet of the present invention in a sealed pouch are as shown in FIG. 8A, in which the sheet is folded in two so that the oily substance absorption layer 1 is on the outside and the aqueous cleansing liquid retention layer 2 is on the inside, and as shown in FIG. 8B, in which the sheet is folded in three. Folding the sheet in three is preferable over folding it in two because the evaporation of the aqueous cleansing liquid can be suppressed better, and because the migration of the powder optionally contained in the aqueous cleansing liquid to the oily substance absorption layer 1 can be suppressed.

When the sheet is folded in three, one of the opposing ends 4a may be overlapped over the other end 4b (not shown). However, it is more preferable for the two ends to be in contact with each other as shown in FIG. 8B.

EXAMPLES

Example 1

A porous polypropylene melt-blown nonwoven fabric with a thickness of 260 μm (Syntex MB; a nonwoven fabric produced by calendering V3030N1 (made by Mitsui Chemical) to a thickness of 80 μm; colored a light pink) was laid over a cotton nonwoven fabric with a basis weight of 40 g/m² (Cottoace C040S/A01, made by Unitika, uncolored), and these were fused together in a stitch pattern by applying a heat sealer from the side of the porous melt-blown nonwoven fabric. The laminate thus obtained was cut to a size of 10 cm×5 cm, and the cotton nonwoven fabric was sprayed with the aqueous lotion in Table 1 below until the absorption reached the percentage shown in Table 3. This yielded a personal cleansing sheet of the two-sided laminate type shown in FIG. 1.

Examples 2 and 3

The single-sided lateral type of personal cleansing sheet shown in FIG. 5 (Example 2), and the checkerboard type of personal cleansing sheet shown in FIG. 7 (Example 3) were obtained in the same manner as in Example 1.

Example 4

A nonwoven fabric with a fiber diameter of 3 μm and a basis weight of 25 g/m² was obtained by melt-blowing a polypropylene (PP) resin. This was calendered at a temperature of 40° C. and a linear pressure of 250 kgf/cm, which yielded a porous polypropylene melt-blown nonwoven fabric with a thickness of 60 μm as the oily substance absorption layer. The air permeability of the nonwoven fabric thus obtained was 0.2 m/kPa.S, and the coefficient of static friction was 0.35.

Over this porous polypropylene melt-blown nonwoven fabric (colored light green) were laid a PP-PE blend polymer film with a basis weight of 40 g/m² (PP:PE=20:80; colored-purple) and a hydrophilic nonwoven fabric with a basis weight of 30 g/m² (a wet-type hydroentangled nonwoven fabric obtained from mixed fiber consisting of {acrylic fiber}:{core/sheath composite fiber (polypropylene (PP) core/polyethylene (PE) sheath)}:{pulp}=45:20:35 (weight ratio)) (hereinafter referred to as V). These were fused together in a stitch pattern by applying a heat sealer from the both sides, and the aqueous lotion (pH=5) shown in Table 2 below was sprayed from the side of the above-mentioned wet-type hydroentangled nonwoven fabric until the absorption reached the percentage shown in Table 3. The laminate thus obtained was cut to a size of 10 cm×5 cm to obtain the personal cleansing sheet shown in FIG. 4.

Comparative Examples 1 to 3

Using the materials shown in Table 3, personal cleansing sheets were fabricated from a single layer of wet sheet (Comparative Example 1), a natural pulp dry sheet (Comparative Example 2), and a soft plastic film (Comparative Example 3).

TABLE 1

| Component | wt % |
| --- | --- |
| Ethanol | 14 |
| Porous nylon powder (Orgasol 2002, made by Elf Atochem) | 3 |
| 1-menthol (cooling agent) | 0.02 |
| Purified water | 82.98 |

TABLE 2

| Component | wt % |
| --- | --- |
| Ethanol | 14 |
| Porous nylon powder (Orgasol 2002, made by Elf Atochem) | 3 |
| 1-menthol (cooling agent) | 0.02 |
| Sodium benzoate | 0.2 |
| Citric acid | 0.1 |
| Purified water | 82.68 |

Evaluation

Using the personal cleansing sheets from the various examples and comparative examples, ten expert panelists removed soils that had stood on the skin, and evaluated the results on the basis of the criteria discussed below for "oily soil cleansing ability," "aqueous soil cleansing ability," "ability of sheet to remove soils," "fresh feel," "feel on the skin," and "ease of visually confirming sebum." For the personal cleansing sheet of Example 4, two additional evaluations were made, "strike-through of aqueous cleansing liquid (liquid strike-through)" and "heat sealability." These evaluation results are given in Table 3.

Oily Soil Cleansing Ability

The inner part of a forearm was coated with a specific amount (W1) of artificial sebum (model sebum soil), the personal cleansing sheet was placed on this coated area so that the oily substance absorption layer thereof would be in contact with the area, the sheet was held down by hand for 5 seconds at a pressure of approximately 9.8 kPa (100 gf/cm²) so as to remove the artificial sebum. The personal cleansing sheet was weighed after this operation, and the cleansing ability was calculated from the following formula (1), in which W2 is the weight of the personal cleansing sheet before cleansing, and W3 is the weight of the personal cleansing sheet after cleansing.

$$\text{Cleansing ability (\%)}=\{(W3-W2)/W1\}\times 100 \qquad (1)$$

The cleansing ability values thus obtained were evaluated on the following scale of A to C.

A: cleansing ability at least 80%
B: cleansing ability at least 50%, less than 80%
C: cleansing ability less than 50%

Aqueous Soil Cleansing Ability

The inner part of a forearm was coated with a specific amount of artificial sweat (model sweat soil), the personal cleansing sheet was placed on this coated area so that the aqueous cleansing liquid retention layer thereof would be in contact with the area, the sheet was held down by hand for 5 seconds at a pressure of approximately 9.8 kPa (100 gf/cm$^2$) so as to remove the artificial sweat. The feel on the skin after cleansing was sensorially evaluated on the following scale of A or C.

A: not sticky (good cleansing)
C: sticky (incomplete cleansing)

Ability of Sheet to Remove Soils

The ability of the sheet to remove oily and aqueous soils was sensorially evaluated on the following scale of A to C.

A: good
B: average
C: poor

Refreshed Feeling

The refreshed feeling was sensorially evaluated on the following scale of A to C.

A: felt refreshed
B: felt somewhat refreshed
C: felt unrefreshed

Skin Feel Upon Use

The feel on the skin was sensorially evaluated on the following scale of A to C.

A: soft
B: fairly soft
C: hard

Liquid Strike-through

A pressure of 4.9 kPa (50 gf/cm$^2$) was applied to the personal cleansing sheet from the oily substance absorption layer side, and the condition of the oily substance absorption layer at this time was visually observed and evaluated on the following scale of A or C.

A: remained dry
C: became wet

Heat Sealability

The personal cleansing sheet was cut to a width of 25 mm, the load required to peel the oily substance absorption layer from the aqueous cleansing liquid retention layer at a rate of 360 mm/min. was measured with a Tensilon tensile tester (RTA-100, made by Orientech), and the results were evaluated on the following scale of A to C.

A: 0.06 N or higher
B: 0.03 N or higher, less than 0.06 N
C: less than 0.03 N

Ease of Visually Confirming Sebum

Artificial skin was uniformly coated with cottonseed oil in an amount of 150 µg/cm$^2$, the cottonseed oil was absorbed by pressing the oily substance absorption layer of the personal cleansing sheet over the oil at a pressure of 4.9 kPa (50 gf/cm$^2$), this portion was visually checked to see whether it could be sufficiently distinguished from its surroundings, and the results were evaluated on the following scale of AA to C.

AA: distinguishable extremely well
A: distinguishable
B: distinguishable somewhat
C: indistinguishable

TABLE 3

|  | Example | | | | Comp. Ex. | | |
| --- | --- | --- | --- | --- | --- | --- | --- |
|  | 1 | 2 | 3 | 4 | 1 | 2 | 3 |
| Relevant figure | FIG. 1 | FIG. 5 | FIG. 7 | FIG. 4 | — | — | — |
| Aqueous lotion absorption (%) | 400 | 400 | 400 | 400 | 400 | — | — |
| Oily substance absorption layer | PP*$^1$ | PP*$^1$ | PP*$^1$ | MB*$^2$ | — | — | PP*$^1$ |
| Liquid impermeable layer | — | — | — | P/E*$^3$ | — | — | — |
| Aqueous cleansing liquid retention layer | CNW*$^4$ | CNW*$^4$ | CNW*$^4$ | V*$^5$ | CNW*$^4$ | — | — |
| Hydrophilic fiber dry sheet | — | — | — | — | — | NP*$^6$ | — |
| Evaluations |  |  |  |  |  |  |  |
| Oily soil cleansing power | A | A | A | A | C | B | A |
| Aqueous soil cleansing power | A | A | A | A | A | C | C |
| Ability of sheet to remove soil | A | A | A | A | A | C | C |
| Fresh feel | A | A | A | A | B | C | C |
| Feel on the skin | A | A | A | A | A | B | B |
| Liquid strike-through | NT*$^7$ | — | — | A | — | — | — |
| Heat sealability | NT*$^7$ | — | — | A | — | — | — |
| Ease of visually confirming sebum | A | AA | AA | AA | C | A | AA |

Table 3 notes
*$^1$PP: A porous polypropylene melt-blown nonwoven fabric with a thickness of 260 µm (Syntex MB; a nonwoven fabric produced by calendering V3030N1 (made by Mitsui Chemical) to a thickness of 80 µm)
*$^2$MB: A calendered porous PP melt-blown nonwoven fabric
*$^3$P/E: PP-PE blend polymer film (PP:PE = 20:80)
*$^4$CNW: A cotton nonwoven fabric with a basis weight of 40 g/m$^2$ (Cottoace C040S/A01, made by Unitika)
*$^5$V: A hydrophilic nonwoven fabric with a basis weight of 30 g/m$^2$
*$^6$NP: Natural pulp with a basis weight of 25 g/m$^2$
*$^7$NT: Not tested As is clear from Table 3, the personal cleansing sheets in Examples 1 to 4 all produced good results for "oily soil cleansing ability," "aqueous soil cleansing ability," "ability of sheet to remove soils," "refreshed feeling," "skin feel upon use," and "ease of visually confirming sebum." The personal cleansing sheet of Example 4, which was provided with a liquid impermeable layer, also had excellent "liquid strike-through" and "heat sealability."

On the other hand, the oily soil cleansing ability was inadequate with the personal cleansing sheet of Comparative Example 1, which did not have an oily substance absorption layer. The single-layer personal cleansing sheet of Comparative Example 2 composed of natural pulp, which did not have an oily substance absorption layer and was not impregnated with an aqueous lotion, produced unsatisfactory results for "aqueous soil cleansing ability," "ability of sheet to remove soils," and "refreshed feeling." The personal cleansing sheet of Comparative Example 3, which was composed of a single layer of an oily substance absorption layer and did not have an aqueous cleansing liquid retention layer, also produced unsatisfactory results for "aqueous soil cleansing ability," "ability of sheet to remove soils," and "refreshed feeling."

The personal cleansing sheet of the present invention allows oily soils such as sebum and aqueous soils such as sweat and salts to be easily washed away from the skin or hair to which these soils have adhered.

The disclosures of the Claims, Specifications, Figures, and Abstracts of Japanese Patent Application No. H11-195145 (filed on Jul. 8, 1999)published as JP200101963, Japanese Patent Application No. 2000-38110 (filed on Feb. 9, 2000)published as JP2001226225, and Japanese Patent Application No. 2000-103498 (filed on Apr. 5, 2000) published as JP2001-286411 are hereby incorporated by reference.

What is claimed is:

1. A personal cleansing sheet, comprising:
   i) a lipophilic region that absorbs oily substances which comprises substantially no liquid; and
   ii) a region that retains an aqueous cleansing liquid which comprises an aqueous skin or hair cleansing liquid.

2. The personal cleansing sheet according to claim 1, wherein the lipophilic region that absorbs oily substances is formed from an oily substance absorption layer, the region that retains an aqueous cleansing liquid is formed from an aqueous cleansing liquid retention layer, and the oily substance absorption layer and the aqueous cleansing liquid retention layer are laminated.

3. The personal cleansing sheet according to claim 2, wherein the oily substance absorption layer is a nonwoven fabric containing lipophilic synthetic fibers.

4. The personal cleansing sheet according to claim 3, wherein the air permeability of said nonwoven fabric is about 0.00005 to about 3 m/kPa.S, and the coefficient of static friction is about 0.2 to about 0.4.

5. The personal cleansing sheet according to claim 3, wherein the basis weight of the nonwoven fabric is about 10 to about 80 g/m$^2$, the apparent density of the nonwoven fabric is about 0.05 to about 0.7 g/cm$^3$, and the diameter of the fibers which make up the nonwoven fabric is about 0.1 to about 10 $\mu$m.

6. The personal cleansing sheet according to claim 2, wherein said oily substance absorption layer and said aqueous cleansing liquid retention layer are each comprised of the same type of thermoplastic resin, and are bonded by heat fusion.

7. The personal cleansing sheet according to claim 2, wherein a liquid impermeable layer is provided between the oily substance absorption layer and the aqueous cleansing liquid retention layer.

8. The personal cleansing sheet according to claim 7, wherein said oily substance absorption layer and said liquid impermeable layer are each comprised of the same type of thermoplastic resin, and are bonded by heat fusion.

9. The personal cleansing sheet according to claim 7, wherein said aqueous cleansing liquid retention layer and said liquid impermeable layer are each comprised of the same type of thermoplastic resin, are bonded by heat fusion.

10. The personal cleansing sheet according to claim 7, wherein said oily substance absorption layer, said aqueous cleansing liquid retention layer, and said liquid impermeable layer are each comprised of the same type of thermoplastic resin, said oily substance absorption layer and said liquid impermeable layer, and said aqueous cleansing liquid retention layer and said liquid impermeable layer are respectively bonded by heat fusion.

11. The personal cleansing sheet according to claim 7, wherein the oily substance absorption layer comprises a melt-blown nonwoven fabric, the liquid impermeable layer comprises a thermoplastic resin film, and the aqueous cleansing liquid retention layer comprises a hydrophilic nonwoven fabric containing thermoplastic resin fibers.

12. The personal cleansing sheet according to claim 11, wherein said oily substance absorption layer comprises a polypropylene melt-blown nonwoven fabric, said liquid impermeable layer comprises a polypropylene-polyethylene blend polymer film and said aqueous cleansing liquid retention layer comprises a hydroentangled nonwoven fabric containing core-sheath composite short fibers, a core of said core-sheath composite short fibers being polypropylene or polyethylene terephthalate and a sheath of said core-sheath composite short fibers being polyethylene.

13. The personal cleansing sheet according to claim 12, wherein said core-sheath composite short fibers are contained in said hydroentangled nonwoven fabric in an amount of about 5 to about 50 wt. %.

14. The personal cleansing sheet according to claim 1, wherein said aqueous cleansing liquid is retained in an amount of from 100 to 500 wt. % based on said region which retains an aqueous cleansing liquid.

15. The personal cleansing sheet according to claim 1, wherein said aqueous cleansing liquid is selected from the group consisting of a lotion, and an emulsion.

16. The personal cleaning sheet according to claim 1, wherein said aqueous cleansing liquid comprises a sebum dissolving component.

17. The personal cleansing sheet according to claim 16, wherein said sebum dissolving component comprises ethanol or a surfactant aqueous solution.

18. The personal cleansing sheet according to claim 1, wherein said aqueous cleansing liquid comprises an insoluble powder.

19. The personal cleansing sheet according to claim 18, wherein said insoluble powder is selected from the group consisting of inorganic powders, organic powders of polymers.

20. The personal cleansing sheet according to claim 19, wherein said insoluble powder is selected from the group consisting of silica, alumina, talc, kaolin, mica, micaceous titanium, zeolite, ultramarine, zinc oxide, iron oxide, nylon powder, vinyl polymer powder, dimethylsilicone crosslinked elastomer powder, polymethyl methacrylate powder, methacrylate-alkylenedimethacrylate copolymer powder and a mixture thereof.

21. The personal cleansing sheet according to claim 18, wherein said insoluble powder has an average particle diameter of about 1 to 30 $\mu$m.

22. The personal cleansing sheet according to claim 18, wherein said insoluble powder is contained in an amount of about 1 to about 40 wt. % based on the weight of said region that retains an aqueous cleansing liquid.

* * * * *